US009895288B2

(12) United States Patent
Augustini et al.

(10) Patent No.: US 9,895,288 B2
(45) Date of Patent: Feb. 20, 2018

(54) FLUID TRANSFER DEVICE

(71) Applicant: Becton Dickinson and Company Limited, Dun Laoghaire (IE)

(72) Inventors: Emily Augustini, Southlake, TX (US); Anam Azimuddin, Spring, TX (US); Katerina Kaczmarski, Raleigh, NC (US); Sae Yong Jang, Seoul (KR); Jiwon Jung, Gyeonggi (KR); Chen Wu, College Station, TX (US)

(73) Assignee: Becton Dickinson and Company Limited, Dun Laoghaire (IE)

( * ) Notice: Subject to any disclaimer, the term of this patent is extended or adjusted under 35 U.S.C. 154(b) by 482 days.

(21) Appl. No.: 14/688,298

(22) Filed: Apr. 16, 2015

(65) Prior Publication Data

US 2015/0297452 A1 Oct. 22, 2015

Related U.S. Application Data

(60) Provisional application No. 61/980,196, filed on Apr. 16, 2014.

(51) Int. Cl.
*A61B 19/00* (2006.01)
*A61J 1/20* (2006.01)

(52) U.S. Cl.
CPC ............. *A61J 1/2048* (2015.05); *A61J 1/201* (2015.05); *A61J 1/2062* (2015.05); *A61J 1/2096* (2013.01); *A61J 1/2089* (2013.01)

(58) Field of Classification Search
CPC ........ A61J 1/2048; A61J 1/201; A61J 1/2062; A61J 1/2096; A61J 1/2089
USPC .................................................. 604/403–416
See application file for complete search history.

(56) References Cited

U.S. PATENT DOCUMENTS

| | | | |
|---|---|---|---|
| 4,436,125 | A | 3/1984 | Blenkush |
| 4,564,054 | A | 1/1986 | Gustavsson |
| 4,673,404 | A | 6/1987 | Gustavsson |
| 4,932,937 | A | 6/1990 | Gustavsson et al. |
| 5,052,725 | A | 10/1991 | Meyer et al. |
| 5,104,158 | A | 4/1992 | Meyer et al. |
| 5,122,129 | A | 6/1992 | Olson et al. |

(Continued)

FOREIGN PATENT DOCUMENTS

| | | | |
|---|---|---|---|
| EP | 2462971 | A1 | 6/2012 |
| WO | 2005011781 | A1 | 2/2005 |

(Continued)

*Primary Examiner* — Philip R Wiest
(74) *Attorney, Agent, or Firm* — The Webb Law Firm

(57) ABSTRACT

A fluid transfer device includes a first portion having a first end and a second end. The first portion includes a first connector configured to be connected to a first container and including a cannula. The fluid transfer device includes a second portion having a first end and a second end. The second end of the first portion extends at least partially into the second end of the second portion. The second portion includes a second connector configured to be connected to a second container and a third connector spaced apart from the second connector. At least a portion of the first portion is axially and rotationally movable with respect to at least a portion of the second portion from a first position in which the first connector is aligned with the second connector to a second position in which the first connector is aligned with the third connector.

20 Claims, 5 Drawing Sheets

(56) References Cited

U.S. PATENT DOCUMENTS

| | | | |
|---|---|---|---|
| 5,280,876 | A | 1/1994 | Atkins |
| 5,290,254 | A | 3/1994 | Vaillancourt |
| 5,322,518 | A | 6/1994 | Schneider et al. |
| 5,334,188 | A | 8/1994 | Inoue et al. |
| 5,360,011 | A | 11/1994 | McCallister |
| 5,395,348 | A | 3/1995 | Ryan |
| 5,437,650 | A | 8/1995 | Larkin et al. |
| 5,464,123 | A | 11/1995 | Scarrow |
| 5,472,430 | A | 12/1995 | Vaillancourt et al. |
| 5,478,328 | A | 12/1995 | Silverman et al. |
| 5,487,728 | A | 1/1996 | Vaillancourt |
| 5,507,733 | A | 4/1996 | Larkin et al. |
| 5,509,911 | A | 4/1996 | Cottone, Sr. et al. |
| 5,545,152 | A | 8/1996 | Funderburk et al. |
| 5,607,392 | A | 3/1997 | Kanner |
| 5,609,584 | A | 3/1997 | Gettig et al. |
| 5,611,792 | A | 3/1997 | Gustafsson |
| 5,647,845 | A | 7/1997 | Haber et al. |
| 5,685,866 | A | 11/1997 | Lopez |
| 5,807,347 | A | 9/1998 | Bonaldo |
| 5,897,526 | A | 4/1999 | Vaillancourt |
| 6,063,068 | A | 5/2000 | Fowles et al. |
| 6,089,541 | A | 7/2000 | Weinheimer et al. |
| 6,113,583 | A | 9/2000 | Fowles et al. |
| 6,132,404 | A | 10/2000 | Lopez |
| 6,139,534 | A | 10/2000 | Niedospial, Jr. et al. |
| 6,221,041 | B1 | 4/2001 | Russo |
| 6,221,056 | B1 | 4/2001 | Silverman |
| 6,343,629 | B1 | 2/2002 | Wessman et al. |
| 6,358,236 | B1 | 3/2002 | DeFoggi et al. |
| 6,409,708 | B1 | 6/2002 | Wessman |
| 6,474,375 | B2 | 11/2002 | Spero et al. |
| 6,478,788 | B1 | 11/2002 | Aneas |
| 6,544,246 | B1 | 4/2003 | Niedospial, Jr. |
| 6,551,299 | B2 | 4/2003 | Miyoshi et al. |
| 6,585,695 | B1 | 7/2003 | Adair et al. |
| 6,599,273 | B1 | 7/2003 | Lopez |
| 6,610,040 | B1 | 8/2003 | Fowles et al. |
| 6,629,958 | B1 | 10/2003 | Spinello |
| 6,656,433 | B2 | 12/2003 | Sasso |
| 6,715,520 | B2 | 4/2004 | Andreasson et al. |
| 6,814,726 | B1 | 11/2004 | Lauer |
| 6,852,103 | B2 | 2/2005 | Fowles et al. |
| 6,875,203 | B1 | 4/2005 | Fowles et al. |
| 6,875,205 | B2 | 4/2005 | Leinsing |
| 6,911,025 | B2 | 6/2005 | Miyahara |
| 6,997,917 | B2 | 2/2006 | Niedospial, Jr. et al. |
| 7,040,598 | B2 | 5/2006 | Raybuck |
| 7,083,605 | B2 | 8/2006 | Miyahara |
| 7,097,209 | B2 | 8/2006 | Unger et al. |
| 7,261,707 | B2 | 8/2007 | Frezza et al. |
| 7,306,584 | B2 | 12/2007 | Wessman et al. |
| 7,326,194 | B2 | 2/2008 | Zinger et al. |
| 7,350,535 | B2 | 4/2008 | Liepold et al. |
| 7,354,427 | B2 | 4/2008 | Fangrow |
| 7,452,349 | B2 | 11/2008 | Miyahara |
| 7,547,300 | B2 | 6/2009 | Fangrow |
| 7,628,772 | B2 | 12/2009 | McConnell et al. |
| 7,648,491 | B2 | 1/2010 | Rogers |
| 7,658,734 | B2 | 2/2010 | Adair et al. |
| 7,743,799 | B2 | 6/2010 | Mosler et al. |
| 7,744,581 | B2 | 6/2010 | Wallen et al. |
| 7,758,560 | B2 | 7/2010 | Connell et al. |
| 7,803,140 | B2 | 9/2010 | Fangrow, Jr. |
| 7,857,805 | B2 | 12/2010 | Raines |
| 7,867,215 | B2 | 1/2011 | Akerlund et al. |
| 7,879,018 | B2 | 2/2011 | Zinger et al. |
| 7,900,659 | B2 | 3/2011 | Whitley et al. |
| 7,927,316 | B2 | 4/2011 | Proulx et al. |
| 7,942,860 | B2 | 5/2011 | Horppu |
| 7,975,733 | B2 | 7/2011 | Horppu et al. |
| 8,096,525 | B2 | 1/2012 | Ryan |
| 8,122,923 | B2 | 2/2012 | Kraus et al. |
| 8,123,738 | B2 | 2/2012 | Vaillancourt |
| 8,137,332 | B2 | 3/2012 | Pipelka |
| 8,167,863 | B2 | 5/2012 | Yaw |
| 8,177,768 | B2 | 5/2012 | Leinsing |
| 8,196,614 | B2 | 6/2012 | Kriheli |
| 8,206,367 | B2 | 6/2012 | Warren et al. |
| 8,211,069 | B2 | 7/2012 | Fangrow, Jr. |
| 8,225,826 | B2 | 7/2012 | Horppu et al. |
| 8,226,628 | B2 | 7/2012 | Muramatsu et al. |
| 8,257,286 | B2 | 9/2012 | Meyer et al. |
| 8,267,127 | B2 | 9/2012 | Kriheli |
| 8,277,424 | B2 | 10/2012 | Pan |
| 8,317,741 | B2 | 11/2012 | Kraushaar |
| 8,317,743 | B2 | 11/2012 | Denenburg |
| 8,398,607 | B2 | 3/2013 | Fangrow, Jr. |
| 8,403,905 | B2 | 3/2013 | Yaw |
| 8,425,487 | B2 | 4/2013 | Beiriger et al. |
| 8,449,521 | B2 | 5/2013 | Thorne, Jr. et al. |
| 8,454,579 | B2 | 6/2013 | Fangrow, Jr. |
| 8,852,145 | B2 * | 10/2014 | Denenburg ........... A61J 1/2096 604/87 |
| 8,979,792 | B2 * | 3/2015 | Lev ....................... A61J 1/2096 604/411 |
| 2002/0087144 | A1 * | 7/2002 | Zinger .................. A61J 1/2089 604/523 |
| 2003/0070726 | A1 | 4/2003 | Andreasson et al. |
| 2005/0065495 | A1 | 3/2005 | Zambaux |
| 2005/0182383 | A1 | 8/2005 | Wallen |
| 2005/0215976 | A1 | 9/2005 | Wallen |
| 2006/0049209 | A1 | 3/2006 | Baker |
| 2007/0079894 | A1 | 4/2007 | Kraus et al. |
| 2008/0045919 | A1 | 2/2008 | Jakob et al. |
| 2008/0287914 | A1 | 11/2008 | Wyatt et al. |
| 2009/0159485 | A1 | 6/2009 | Jakob et al. |
| 2010/0179506 | A1 | 7/2010 | Shemesh et al. |
| 2010/0217226 | A1 | 8/2010 | Shemesh |
| 2011/0004183 | A1 | 1/2011 | Carrez et al. |
| 2011/0062703 | A1 | 3/2011 | Lopez et al. |
| 2011/0074148 | A1 | 3/2011 | Imai |
| 2011/0106046 | A1 | 5/2011 | Hiranuma et al. |
| 2011/0178493 | A1 * | 7/2011 | Okiyama .............. A61J 1/2089 604/406 |
| 2011/0257621 | A1 | 10/2011 | Fangrow |
| 2011/0291406 | A1 | 12/2011 | Kraft et al. |
| 2012/0035580 | A1 | 2/2012 | Fangrow |
| 2012/0046636 | A1 | 2/2012 | Kriheli |
| 2012/0123381 | A1 | 5/2012 | Kraus et al. |
| 2012/0192968 | A1 | 8/2012 | Bonnal et al. |
| 2012/0192976 | A1 | 8/2012 | Rahimy et al. |
| 2012/0203193 | A1 | 8/2012 | Rogers |
| 2012/0265163 | A1 | 10/2012 | Cheng et al. |
| 2012/0279884 | A1 | 11/2012 | Tennican et al. |
| 2012/0316536 | A1 | 12/2012 | Carrez et al. |
| 2013/0006211 | A1 | 1/2013 | Takemoto |
| 2013/0012908 | A1 | 1/2013 | Yeung |
| 2013/0066293 | A1 | 3/2013 | Garfield et al. |
| 2013/0072893 | A1 * | 3/2013 | Takemoto ............. A61J 1/2096 604/403 |
| 2013/0076019 | A1 | 3/2013 | Takemoto |
| 2013/0079744 | A1 | 3/2013 | Okiyama et al. |

FOREIGN PATENT DOCUMENTS

| | | | |
|---|---|---|---|
| WO | 2006103074 | A1 | 10/2006 |
| WO | 2009024807 | A1 | 2/2009 |
| WO | 2009090627 | A1 | 7/2009 |
| WO | 2011050333 | A1 | 4/2011 |
| WO | 2012069401 | A1 | 5/2012 |
| WO | 2012119225 | A1 | 9/2012 |
| WO | 2012168235 | A1 | 12/2012 |
| WO | 2013025946 | A1 | 2/2013 |
| WO | 2013054323 | A1 | 3/2013 |
| WO | 2013066779 | A1 | 5/2013 |
| WO | 2013115730 | A1 | 8/2013 |
| WO | 2013179596 | A1 | 12/2013 |
| WO | 2014122643 | A1 | 8/2014 |
| WO | 2014181320 | A1 | 11/2014 |

* cited by examiner

FLUID TRANSFER DEVICE

CROSS-REFERENCE TO RELATED APPLICATION

This application claims priority to U.S. Provisional Application Ser. No. 61/980,196, filed Apr. 16, 2014, which is hereby incorporated by reference in its entirety.

BACKGROUND OF THE INVENTION

Field of the Invention

The present invention relates to a device for transferring fluid from a container to another container or device. More particularly, the present invention relates to a device that provides a closed environment for transferring fluid from a container to another container.

Description of Related Art

Health care providers reconstituting, transporting, and administering hazardous drugs, such as cancer treatments, can put health care providers at risk of exposure to these medications and present a major hazard in the health care environment. For example, nurses treating cancer patients risk being exposed to chemotherapy drugs and their toxic effects. Unintentional chemotherapy exposure can affect the nervous system, impair the reproductive system, and bring an increased risk of developing blood cancers in the future. In order to reduce the risk of health care providers being exposed to toxic drugs, the closed transfer of these drugs becomes important.

Some drugs must be dissolved or diluted before they are administered, which involves transferring a solvent from one container to a sealed vial containing the drug in powder or liquid form, by means of a needle. Closed-system transfer devices (CSTDs) are used to prevent such hazardous exposure. However, currently available CSTDs are often complicated and/or costly to manufacture and may be complicated for the healthcare workers to operate. Therefore, there is a need for a CSTD that is easier and more economical to manufacture and easier for healthcare workers to use.

SUMMARY OF THE INVENTION

In accordance with an aspect of the present invention, a fluid transfer device includes a first portion having a first end and a second end. The first portion includes a first connector configured to be connected to a first container and including a cannula. The fluid transfer device includes a second portion having a first end and a second end. The second end of the first portion extends at least partially into the second end of the second portion. The second portion includes a second connector configured to be connected to a second container and a third connector spaced apart from the second connector. At least a portion of the first portion is axially and rotationally movable with respect to at least a portion of the second portion from a first position in which the first connector is aligned with the second connector to a second position in which the first connector is aligned with the third connector.

The first and second portions may be cylindrical. The first end of the first portion may be closed and the second end of the first portion may be open. The first end of the second portion may be closed and the second end of the second portion may be open.

The fluid transfer device may further include a sealing member disposed between a portion of the first portion and a portion of the second portion. The sealing member may be positioned within a groove defined by the first portion.

The fluid transfer device may include a container sealably engageable with the second connector. The container may be a flexible container.

The first connector may be a luer fitting and configured to be connected to a syringe. The second connector may be a snap fit connection configured to secure the second connector to a vial. The third connector may be configured to connect to an IV adapter.

When the first portion is in the first position and axially advanced into the second portion, the cannula of the first connector may be in fluid communication with the second connector. When the first portion is in the second position and axially advanced into the second portion, the cannula of the first connector may be in fluid communication with the third connector.

The first portion and the second portion may define a chamber, with the first portion axially movable with respect to the second portion from a first position in which the chamber defines a first volume, to a second position in which the chamber defines a second volume, the first volume greater than the second volume.

The fluid transfer device may include a handle extending from a portion of the first portion for transitioning the first portion from the first position to the second position.

The third connector may define a passageway, with the third connector including a seal configured to seal the passageway of the third connector.

In a further aspect, a method of transferring a fluid includes: providing a fluid transfer device having a first portion, a second portion where the first portion extends at least partially into the second portion, a first connector comprising a cannula with the first connector connected to the first portion, a second connector connected to the second portion, and a third connector defined within the second portion and spaced apart from the second connector, where at least a portion of the first portion is movable axially and rotationally with respect to at least a portion of the second portion; engaging a first device with the first connector, engaging a second device with the second connector, and engaging a third device with the third connector; advancing a portion of the first portion into a portion of the second portion until the cannula provides fluid communication between the first device and the second device; withdrawing a portion of the first portion from a portion of the second portion; rotating the first portion with respect to the second portion until the first connector is aligned with the third connector; and advancing a portion of the first portion into a portion of the second portion until the cannula provides fluid communication between the first device and the third device.

The first device may be a syringe, the second device may be a vial, and the third device may be an IV adapter.

The method may further include: providing a container having an open end and a closed end; placing the container around the second device after connecting the second device to the second connector; and sealably connecting the open end of the container around the second connector.

The method may also include piercing a seal positioned adjacent to a passageway of the third connector with the cannula.

In a further aspect, a fluid transfer device includes a first portion including a first connector configured to be connected to a first container, and a second portion including a second connector configured to be connected to a second container and a third connector spaced apart from the second connector, with the first connector rotatable relative to the second connector and the third connector. The first and second portions have a first position in which the first connector is aligned with the second connector and a second position in which the first connector is aligned with the third connector, where at least a portion of the first portion is axially movable with respect to at least a portion of the second portion.

DESCRIPTION OF THE INVENTION

Figure 1:
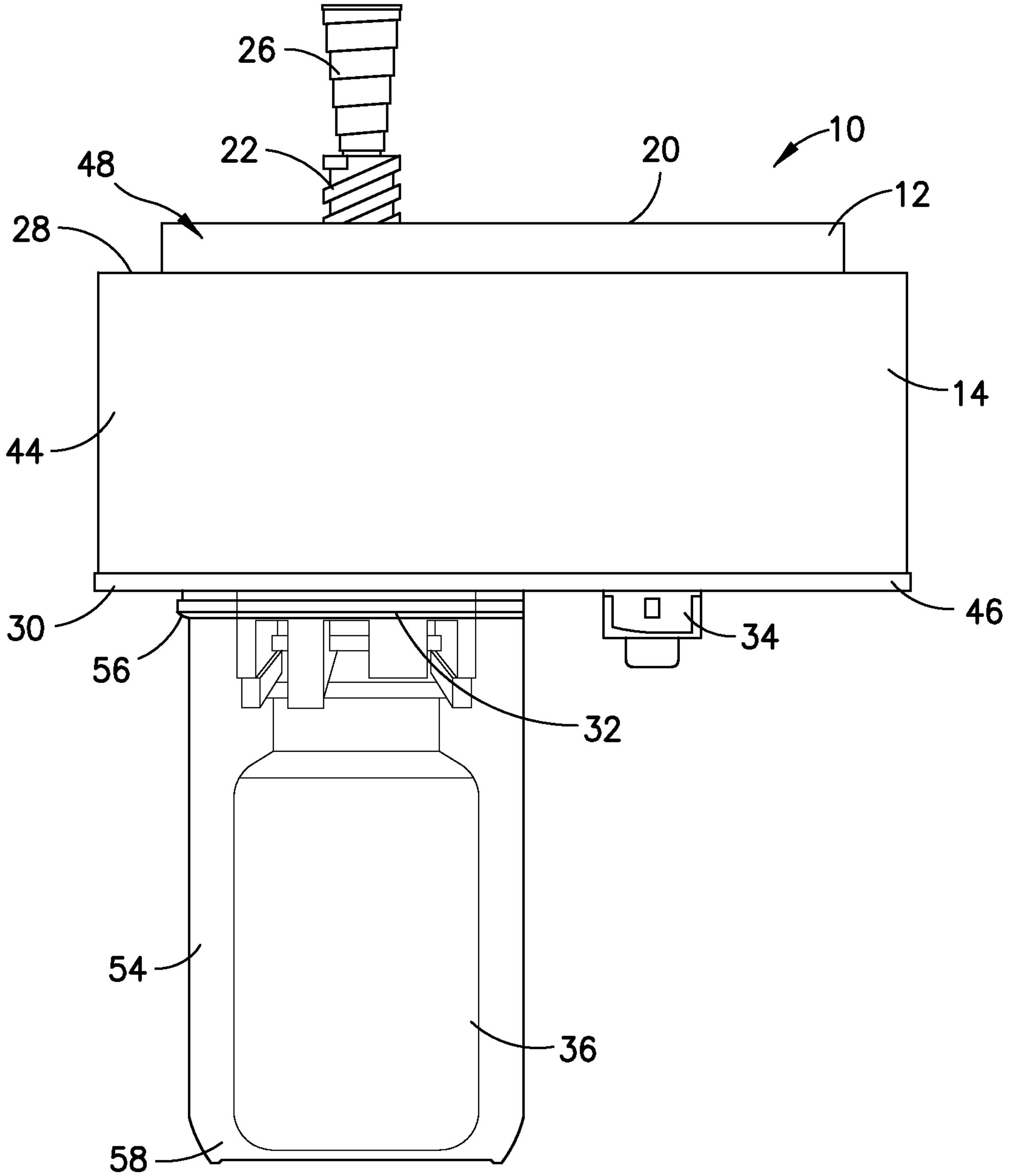
FIG. 1 is a side view of a fluid transfer device according to one aspect of the present invention.

For purposes of the description hereinafter, the words “upper”, “lower”, “right”, “left”, “vertical”, “horizontal”, “top”, “bottom”, “lateral”, “longitudinal”, and like spatial terms, if used, shall relate to the described aspects as oriented in the drawing figures. However, it is to be understood that many alternative variations and aspects may be assumed except where expressly specified to the contrary. It is also to be understood that the specific devices and aspects illustrated in the accompanying drawings and described herein are simply exemplary aspects of the invention.

A fluid transfer device of the present invention is used to provide transfer, including reconstitution if necessary, of a fluid medicament from a first container, often a vial, to a patient in a completely closed system such that the medicament is never released into the atmosphere.

As shown in FIGS. 1-7, the fluid transfer device 10 has a first cylindrical portion 12, a second cylindrical portion 14, and at least one sealing member 16 provided between the first cylindrical portion 12 and the second cylindrical portion 14.

The first cylindrical portion 12 has an open end 18 and a closed end 20. A first connector 22 including a central passageway therethrough extends from the closed end 20 of the first cylindrical portion 12. A needle cannula 24 is provided in fluid communication with the central passageway of the first connector 22 and may extend into the interior of the first cylindrical portion 12. The first cylindrical portion 12 may also include a handle 23 extending from the first cylindrical portion 12, such as from the closed end 20, which is shown in FIGS. 2-7, but not FIG. 1.

The first connector 22 may be configured to connect to a syringe 26 and may be a standard male luer fitting that can cooperate with a corresponding female luer fitting on the syringe 26 to attach the syringe 26 to the first cylindrical portion 12 as shown in FIG. 1, or may be a standard female luer fitting that can cooperate with a corresponding male luer fitting on the syringe 26, although other suitable connectors may be utilized. The needle cannula 24 is connected to the first connector 22 such that the central passageway of the first connector 22 is sealingly engaged with the needle cannula 24 to provide an air-tight and fluid-tight connection therebetween.

The second cylindrical portion 14 has an open end 28 and a closed end 30. A second connector 32 including a central passageway therethrough extends from the second cylindrical portion 14, such as the closed end 30 of the second cylindrical portion 14. A third connector 34 including a central passageway therethrough also extends from the closed end 30 of the second cylindrical portion 14 and is spaced apart from the second connector 32.

The second connector 32 may be adapted for connection to a medicament container 36 that contains a medicament. The container 36 may be a vial having a pierceable septum, as shown in FIGS. 2-7. The second connector 32 may be a threaded connector as shown in FIGS. 3-7 or, as shown in FIG. 1, may be a snap-fit connector having vial grip members, hook protrusions, and angled walls, or other suitable connectors. The second connector 32 may include a seal 38, such as an O-ring, to provide a sealing engagement between the container 36 and the second connector 32.

The third connector 34 may be adapted for connection to an IV adapter 40 through which the medicament will be administered to the patient. Such a connector may be any standard connector known in the art including, but not limited to, a connector having a groove including a locking portion wherein the IV adapter 40 has protrusions for engagement with the groove or a connector having protrusions wherein the IV adapter 40 has a groove including a locking portion for engagement with the protrusions. The third connector 34 may further include a seal 42, such as an elastomeric seal or the like. The seal 42 may be air-tight and fluid-tight and adapted to seal the central passageway of the third connector 34. Such a seal may also be adapted to allow the passage of the needle cannula 24 through the seal 42 in a manner in which the seal 42 provides an air-tight and fluid-tight seal around the needle cannula 24 and, on removal of the needle cannula 24 from the seal 42, reseals to provide an air-tight and fluid-tight seal for the central passageway of the third connector 34.

The first cylindrical portion 12 and/or the second cylindrical portion 14 may each be formed of a single piece or may comprise a sidewall portion 44 and a closure portion 46 as shown in FIGS. 1-7. The sidewall portion 44 and closure portion 46 may be connected using a suitable means that provides an air-tight and fluid-tight seal including, but not limited to, welding or adhesive.

The outer diameter of the first cylindrical portion 12 is slightly less than the inner diameter of the second cylindrical portion 14 such that a portion of the open end 18 of the first cylindrical portion 12 extends into a portion of the open end 28 of the second cylindrical portion 14. In this manner, the first cylindrical portion 12 and the second cylindrical portion

14 define an internal chamber. The needle cannula 24 is contained within this chamber.

The first connector 22, the second connector 32, and the third connector 34 are positioned such that the first connector 22 can be axially aligned with either the second connector 32, or the third connector 34 when the first cylindrical portion 12 is mated with the second cylindrical portion 14 and rotated with respect to the second cylindrical portion 14.

The first cylindrical portion 12 is movable axially and rotationally with respect to the second cylindrical portion 14. The first cylindrical portion 12 is axially movable with respect to the second cylindrical portion 14 from a first position (shown in FIGS. 3, 5, and 6) to a second position (shown in FIGS. 1, 4, and 7) where the volume of the chamber in the first position is greater than the volume of the chamber in the second position. In addition, the first cylindrical portion 12 is rotatable with respect to the second cylindrical portion 14 from a first position (shown in FIGS. 1 and 3-5) where the first connector 22 is aligned with the second connector 32 to a second position (shown in FIGS. 6 and 7) where the first connector 22 is aligned with the third connector 34.

Figure 2:
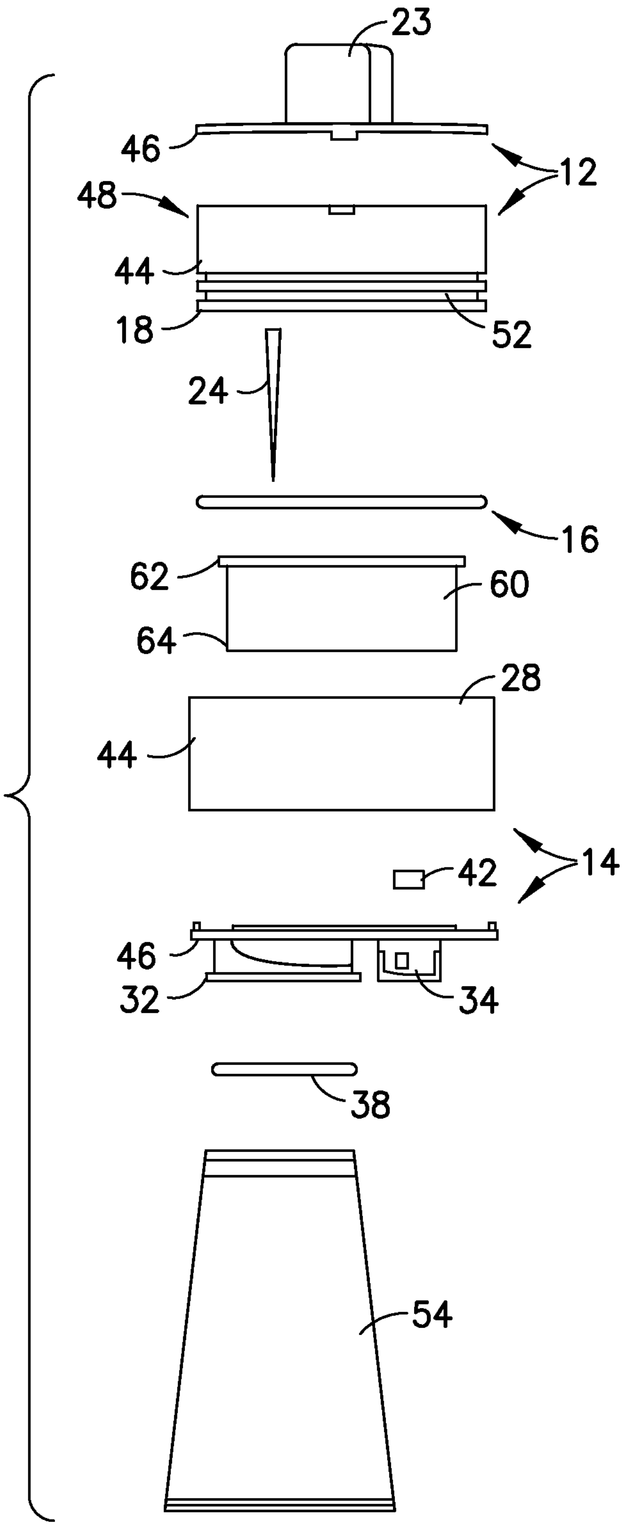
FIG. 2 is an exploded perspective view of the fluid transfer device of FIG. 1 according to one aspect of the present invention.

The sealing member 16 is provided between an outer sidewall surface 48 of the first cylindrical portion 12 and an inner sidewall surface of the second cylindrical portion 14. As shown in FIG. 2, the sealing member 16 may be an O-ring and may sit in a groove 52 in the outer sidewall surface 48 of the first cylindrical portion 12 or the inner sidewall surface of the second cylindrical portion 14. A second sealing member 16 may also be provided. The sealing member 16 is adapted to provide an air-tight and fluid-tight seal between the first cylindrical portion 12 and the second cylindrical portion 14 yet still allow for the axial and rotational movement of the first cylindrical portion 12 with respect to the second cylindrical portion 14.

A container 54 having an open end 56 and a closed end 58 may also be provided. The open end 56 of the container 54 is sealably connected around the second connector 32. The connection between the second connector 32 and the open end 56 of the container 54 may be a threaded connection or may utilize an elastic band that stretches over the container 54 and fits into a groove in the second connector 32, although any suitable connection that provides an air-tight and fluid-tight seal may be used.

The container 54 may be flexible and may be made of plastic or any suitable material that allows it to be fit over the medicament container 36 that contains the medicament and sealed to the second connector 32. The container 54 may be a plastic bag.

Figure 4:
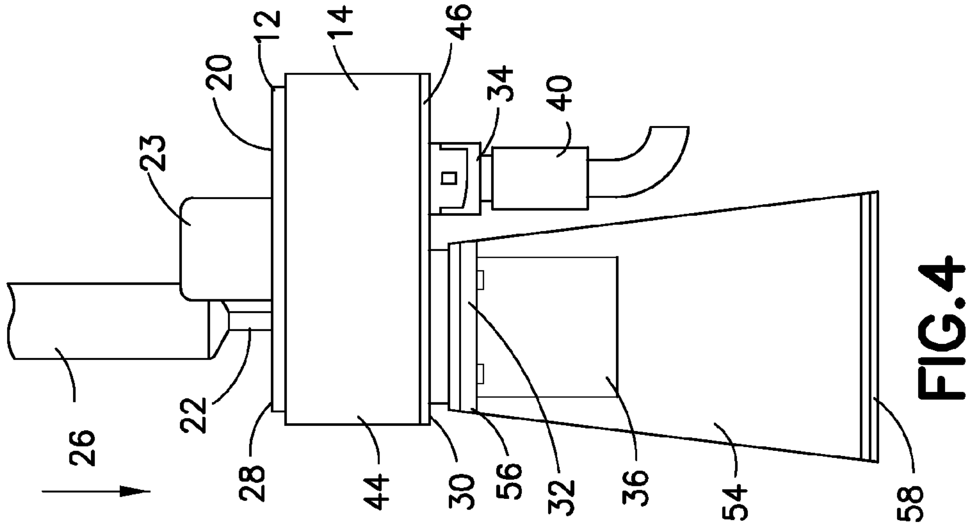
FIG. 4 is a side view of the fluid transfer device of FIG. 3 after the first portion has been pushed into the second portion to establish fluid communication between the syringe and the medicament container according to one aspect of the present invention.
Figure 6:
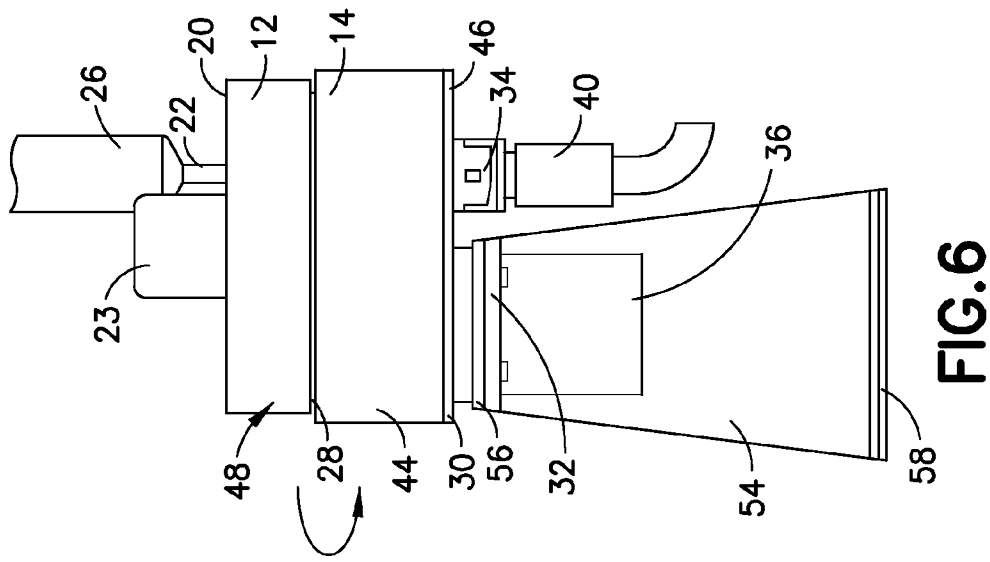
FIG. 6 is a side view of the fluid transfer device of FIG. 5 after the first portion has been rotated with respect to the second portion to align the syringe with the IV adapter according to one aspect of the present invention.
Figure 7:
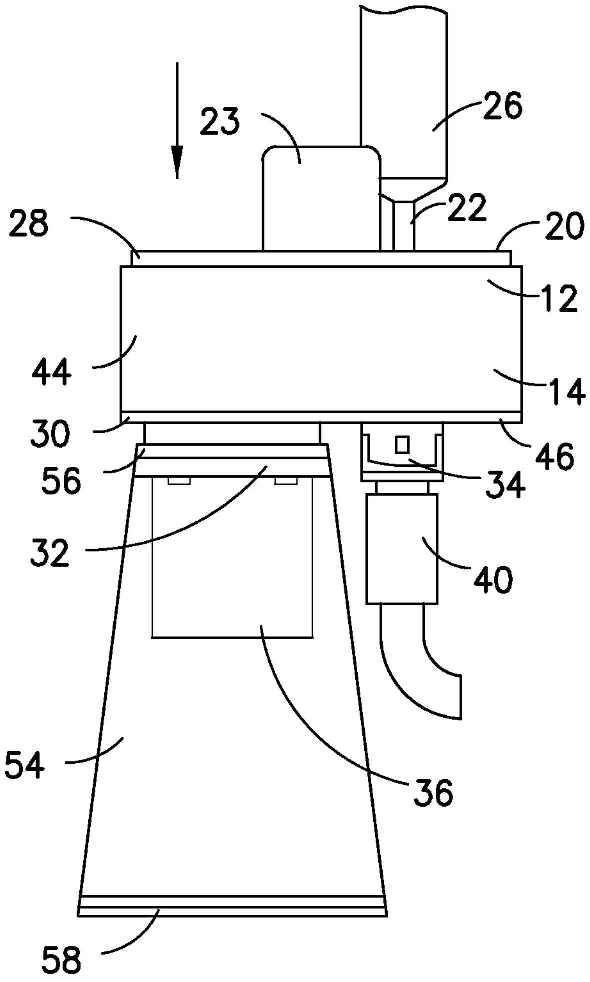
FIG. 7 is a side view of the fluid transfer device of FIG. 6 after the first portion has been pushed into the second portion to establish fluid communication between the syringe and the IV adapter according to one aspect of the present invention.

The fluid transfer device 10 may also include a third cylindrical portion 60 having a first open end 62 and a second open end 64. The third cylindrical portion 60 has an outer diameter that is smaller than the inner diameter of the first cylindrical portion 12 and the second cylindrical portion 14. The first open end 62 of the third cylindrical portion 60 abuts the closed end 20 of the first cylindrical member 12 and the second open end 64 of the third cylindrical portion 60 abuts the closed end 30 of the second cylindrical member 14 when the first cylindrical portion 12 is advanced into the second cylindrical portion 14 as shown in FIGS. 1, 4, and 7. This results in a more equal distribution of force during this operation. In addition, the third cylindrical portion 60 stabilizes the device during rotation of the first cylindrical portion 12 with respect to the second cylindrical portion 14 as shown in FIG. 6. All of the components including the first cylindrical portion 12, the second cylindrical portion 14, the first connector 22, the second connector 32, the third connector 34, and the container 54 may be made from any suitable material having the necessary chemical resistance and strength including, but not limited to, polypropylene (PP) and polyvinyl chloride (PVC).

Figure 3:
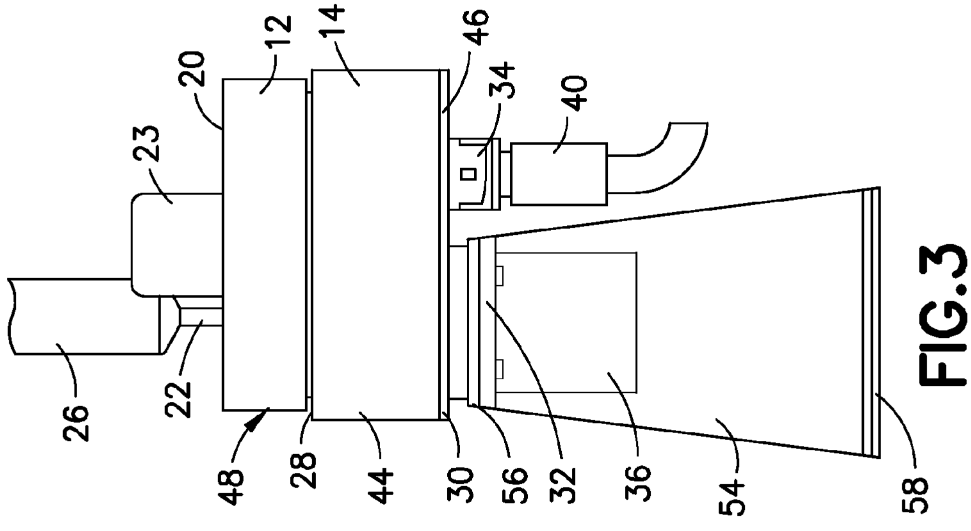
FIG. 3 is a side view of the fluid transfer device of FIG. 1 in an initial position according to one aspect of the present invention.

In use, as shown in FIG. 3, the fluid transfer device 10 is placed in a first position where the first connector 22 is axially aligned with the second connector 32 and the first cylindrical portion 12 extends from the second cylindrical portion 14. A first device, such as a syringe 26 having a diluent, is connected to the first connector 22. A second device, such as a medicament container 36, is connected to the second connector 32. A third device, such as IV adapter 40 or other device for delivery of the medicament to the patient, is connected to the third connector 34. The container 54 may then be placed over the medicament container 36 and sealingly secured to the second connector 32.

As shown in FIG. 4, by actuating the handle 23, the first cylindrical portion 12 is at least partially advanced into the second cylindrical portion 14 reducing the volume of the chamber and causing the needle cannula 24 to enter the medicament container 36 creating a fluid passageway between the syringe 26, connected to the first connector 22, and the medicament container 36, connected to the second connector 32. The needle cannula 24 may enter the medicament container 36 by piercing a septum on the top of the medicament container 36 or any other arrangement as long as a fluid passageway is provided between the syringe 26 and the medicament container 36. At this point, if the medicament is ready for administration to the patient, it can be drawn into the syringe 26. If the medicament is a powder or liquid that needs to be reconstituted, the necessary fluid/solvent can be injected into the medicament container 36 from the syringe 26 and, upon completion of the reconstitution, the medicament can be drawn into the syringe 26.

Figure 5:
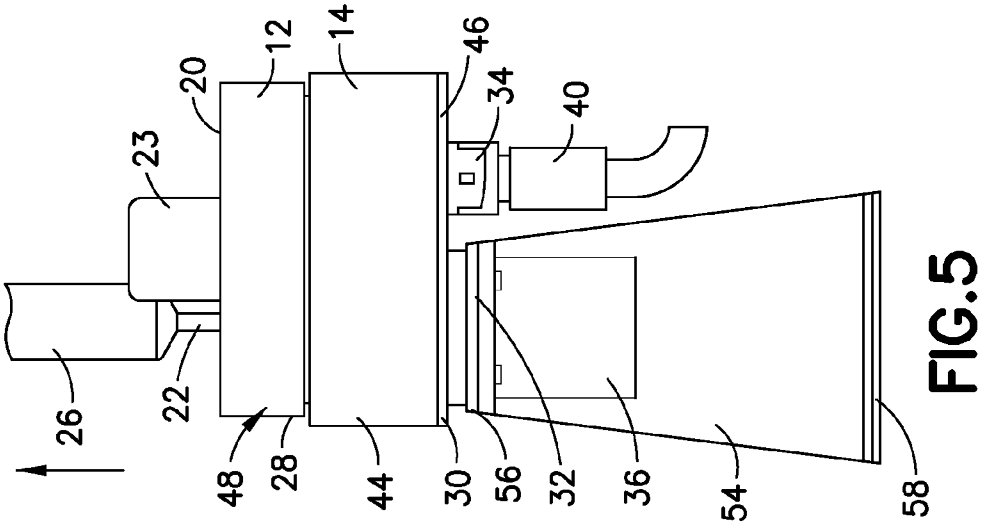
FIG. 5 is a side view of the fluid transfer device of FIG. 4 after the first portion has been withdrawn from the second portion to disengage fluid communication between the syringe and the medicament container according to one aspect of the present invention.

As shown in FIG. 5, after the medicament has been drawn into the syringe 26, the first cylindrical portion 12 is at least partially withdrawn from the second cylindrical portion 14, such as by actuating the handle 23, thus increasing the volume of the chamber defined between the first cylindrical portion 12 and the second cylindrical portion 14. As the first cylindrical portion 12 is partially displaced from the second cylindrical portion 14, the needle cannula 24 is removed from the medicament container 36. Then, as shown in FIG. 6, the first cylindrical portion 12 is rotated with respect to the second cylindrical portion 14 until the first connector 22 is axially aligned with the third connector 34. After rotation of the first cylindrical portion 12, as shown in FIG. 7, a portion of the first cylindrical portion 12 is again pushed into the second cylindrical portion 14 reducing the volume of the chamber defined between the first cylindrical portion 12 and the second cylindrical portion 14, thereby causing the needle cannula 24 to enter the IV adapter 40 creating a fluid passageway between the syringe 26 connected to the first connector 22 and the IV adapter 40 connected to the third connector 34. At this point, the medicament can be injected from the syringe 26 into the IV tube for delivery to the patient. This procedure may be repeated until all the medicament has been delivered to the patient.

The fluid transfer device 10 has at least two advantages over prior closed system transfer devices. First, the number of components is reduced resulting in a corresponding reduction in manufacturing costs. Second, the entire drug reconstitution process and transfer of the drug to the IV bag is contained within one component, so the number of different devices that the user must use to complete this process and the number of actions the user must perform is reduced as compared to prior art transfer devices.

While the present invention is described with reference to several distinct aspects of a fluid transfer device and method of use, those skilled in the art may make modifications and alterations without departing from the scope and spirit. Accordingly, the above detailed description is intended to be illustrative rather than restrictive.

The invention claimed is:

1. A fluid transfer device comprising:

a first portion having a first end and a second end, the first portion including a first connector configured to be connected to a first container, the first connector comprising a cannula; and a second portion having a first end and a second end, wherein the second end of the first portion extends at least partially into the second end of the second portion, the second portion including a second connector configured to be connected to a second container and a third connector spaced apart from the second connector, wherein at least a portion of the first portion is axially and rotationally movable with respect to at least a portion of the second portion from a first position in which the first connector is aligned with the second connector to a second position in which the first connector is aligned with the third connector.

2. The fluid transfer device of claim 1, wherein the first and second portions are cylindrical.

3. The fluid transfer device of claim 1, wherein the first end of the first portion is closed and the second end of the first portion is open.

4. The fluid transfer device of claim 3, wherein the first end of the second portion is closed and the second end of the second portion is open.

5. The fluid transfer device of claim 1, further comprising a sealing member disposed between a portion of the first portion and a portion of the second portion.

6. The fluid transfer device of claim 5, wherein the sealing member is positioned within a groove defined by the first portion.

7. The fluid transfer device of claim 1, further comprising a container sealably engageable with the second connector.

8. The fluid transfer device of claim 7, wherein the container is a flexible container.

9. The fluid transfer device of claim 1, wherein the first connector is a luer fitting and configured to be connected to a syringe.

10. The fluid transfer device of claim 1, wherein the second connector comprises a snap fit connection configured to secure the second connector to a vial.

11. The fluid transfer device of claim 1, wherein the third connector is configured to connect to an IV adapter.

12. The fluid transfer device of claim 1, wherein, when the first portion is in the first position and axially advanced into the second portion, the cannula of the first connector is in fluid communication with the second connector.

13. The fluid transfer device of claim 12, wherein, when the first portion is in the second position and axially advanced into the second portion, the cannula of the first connector is in fluid communication with the third connector.

14. The fluid transfer device of claim 1, wherein the first portion and the second portion define a chamber, and wherein the first portion is axially movable with respect to the second portion from a first position in which the chamber defines a first volume, to a second position in which the chamber defines a second volume, the first volume greater than the second volume.

15. The fluid transfer device of claim 14, further comprising a handle extending from a portion of the first portion for transitioning the first portion from the first position to the second position.

16. The fluid transfer device of claim 1, wherein the third connector defines a passageway, the third connector comprising a seal configured to seal the passageway of the third connector.

17. A method of transferring a fluid comprising:

providing a fluid transfer device comprising:

a first portion, a second portion, the first portion extending at least partially into the second portion, a first connector comprising a cannula, the first connector connected to the first portion, a second connector connected to the second portion, and a third connector defined within the second portion and spaced apart from the second connector, wherein at least a portion of the first portion is movable axially and rotationally with respect to at least a portion of the second portion;

engaging a first device with the first connector, engaging a second device with the second connector, and engaging a third device with the third connector;

advancing a portion of the first portion into a portion of the second portion until the cannula provides fluid communication between the first device and the second device;

withdrawing a portion of the first portion from a portion of the second portion;

rotating the first portion with respect to the second portion until the first connector is aligned with the third connector; and advancing a portion of the first portion into a portion of the second portion until the cannula provides fluid communication between the first device and the third device.

18. The method of claim 17, wherein the first device is a syringe, the second device is vial, and the third device is an IV adapter.

19. The method of claim 17, further comprising:

providing a container having an open end and a closed end;

placing the container around the second device after connecting the second device to the second connector; and sealably connecting the open end of the container around the second connector.

20. A fluid transfer device comprising:

a first portion including a first connector configured to be connected to a first container; and a second portion including a second connector configured to be connected to a second container and a third connector spaced apart from the second connector, the first connector rotatable relative to the second connector and the third connector, wherein the first and second portions have a first position in which the first connector is aligned with the second connector and a second position in which the first connector is aligned with the third connector, at least a portion of the first portion is axially movable with respect to at least a portion of the second portion.

* * * * *